United States Patent
Wong et al.

[11] Patent Number: 5,869,079
[45] Date of Patent: Feb. 9, 1999

[54] FORMULATION FOR CONTROLLED RELEASE OF DRUGS BY COMBINING HYDROPHILIC AND HYDROPHOBIC AGENTS

[75] Inventors: Vernon Wong, Rockville, Md.; Frank Kochinke, San Jose, Calif.

[73] Assignee: Oculex Pharmaceuticals, Inc., Sunnyvale, Calif.

[21] Appl. No.: 459,134

[22] Filed: Jun. 2, 1995

[51] Int. Cl.[6] ............... A61K 47/34; A61K 47/36; A61K 9/10
[52] U.S. Cl. ............ 424/426; 424/423; 514/953
[58] Field of Search ................ 424/422, 423, 424/426, 486, 488; 514/953

[56] References Cited

U.S. PATENT DOCUMENTS

| | | | |
|---|---|---|---|
| 4,478,818 | 10/1984 | Shell et al. | 424/426 |
| 4,997,652 | 3/1991 | Wong | 424/428 |
| 5,075,115 | 12/1991 | Brine | 424/486 |
| 5,164,188 | 11/1992 | Wong | 424/428 |
| 5,356,629 | 10/1994 | Sander et al. | 424/426 |
| 5,385,887 | 1/1995 | Yim et al. | 424/426 |

OTHER PUBLICATIONS

R. Baker, "Controlled Release of Biologically Active Agents," *A Wiley–Interscience Publication*, p. 73 (1987).

Heller, Biodegradable Polymers in Controlled Drug Delivery (1987) *CRC Critical Reviews in Therapeutic Drug Carrier Systems*, vol. 1, Issue 1:39–90.

Miller et al., Degradation Rates of Oral Resorbable Implants (Polylactates and Polyglycolates): Rate Modification with Changes in PLA/PGA Copolymer Ratios (1977) *J. Biomed. Mater. Res.*, vol. 11:711–719.

Di Colo, Controlled Drug Release From Implantable Matrices Based On Hydrophobic Polymers (1992) *Biomaterials*, vol. 13, No. 12:850–856.

Jackanicz et al., Polyactic Acid As A Biogradable Carrier For Contraceptive Steroids (1973) *Contraception*, vol. 8, No. 3:227–235.

*Primary Examiner*—Edward J. Webman
*Attorney, Agent, or Firm*—Flehr Hohbach Test Albritton & Herbert, LLP

[57] ABSTRACT

Combinations of hydrophilic and hydrophobic entities in a biodegradable sustained release implant are shown to modulate each other's rate of release. Formulations of a therapeutically active agent and modulator provide controlled, sustained drug release for an extended period of time.

1 Claim, 3 Drawing Sheets

FORMULATION FOR CONTROLLED RELEASE OF DRUGS BY COMBINING HYDROPHILIC AND HYDROPHOBIC AGENTS

TECHNICAL FIELD

Biodegradable implants formulated for controlled, sustained drug release.

BACKGROUND OF THE INVENTION

Solid pharmaceutically active implants that provide sustained release of an active ingredient are able to provide a relatively uniform concentration of active ingredients in the body. Implants are particularly useful for providing a high local concentration at a particular target site for extended periods of time. These sustained release forms reduce the number of doses of the drug to be administered, and avoid the peaks and troughs of drug concentration found with traditional drug therapies. Use of a biodegradable drug delivery system has the further benefit that the spent implant need not be removed from the target site.

Many of the anticipated benefits of delayed release implants are dependent upon sustained release at a relatively constant level. However, formulations of hydrophobic drugs with biodegradable matrices may have a release profile which shows little or no release until erosion of the matrix occurs, at which point there is a dumping of drug.

The eye is of particular interest when formulating implantable drugs, because one can reduce the amount of surgical manipulation required, and provide effective levels of the drug specifically to the eye. When a solution is injected directly into the eye, the drug quickly washes out or is depleted from within the eye into the general circulation. From the therapeutic standpoint, this may be as useless as giving no drug at all. Because of this inherent difficulty of delivering drugs into the eye, successful medical treatment of ocular diseases is inadequate.

Improved sustained release formulations which allow for a constant drug release rate are of considerable interest for medical and veterinary uses.

Relevant Literature

U.S. Pat. Nos. 4,997,652 and 5,164,188 disclose biocompatible implants for introducing into an anterior chamber or posterior segment of an eye for the treatment of an ocular condition.

Heller, *Biodegradable Polymers in Controlled Drug Delivery*, in: CRC Critical Reviews in Therapeutic Drug Carrier Systems, Vol. 1, CRC Press, Boca Raton, Fla., 1987, pp 39–90, describes encapsulation for controlled drug delivery. Heller in: Hydrogels in Medicine and Pharmacy, N. A. Peppes ed., Vol. III, CRC Press, Boca Raton, Fla., 1987, pp 137–149, further describes bioerodible polymers.

Anderson et al., *Contraception* (1976) 13:375 and Miller et al., *J. Biomed. Materials Res.* (1977) 11:711, describe various properties of poly(dL-lactic acid). U.S. Pat. No. 5,075,115 discloses sustained release formulations with lactic acid polymers and co-polymers.

Di Colo (1992) *Biomaterials* 13:850–856 describes controlled drug release from hydrophobic polymers.

SUMMARY OF THE INVENTION

Compositions and methods are provided for biodegradable implants formulated to provide a controlled, sustained drug release. The release rate is modulated by combining in the implant hydrophobic and hydrophilic agents. The release modulator may act to accelerate or retard the rate of release. Optionally, the modulator will be a therapeutically active agent. The invention provides a sustained release implant having a combination of active agents with a defined release profile.

DESCRIPTION OF THE SPECIFIC EMBODIMENTS

Figure 1A:
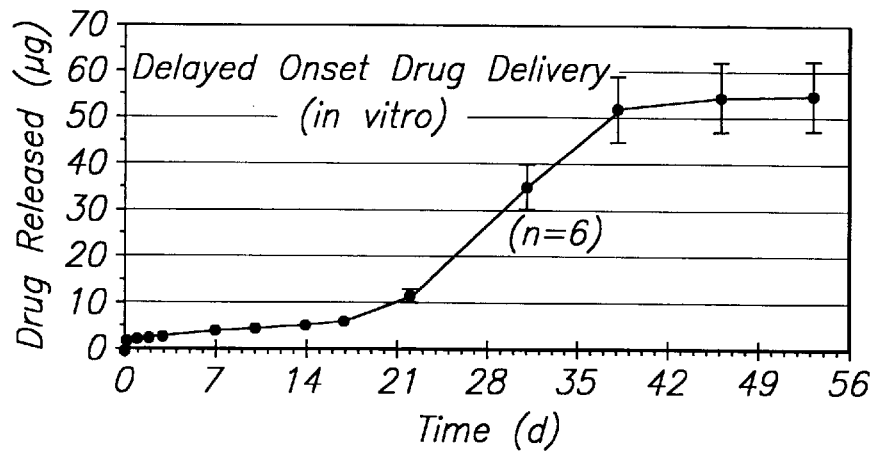
FIG. 1A shows the release profile of a hydrophobic drug from an extended release drug delivery system.

A controlled drug release is achieved by an improved formulation of slow release biodegradable implants. The release rate of a drug from an implant is modulated by addition of a release modulator to the implant. Release of a hydrophobic agent is increased by inclusion of an accelerator in the implant, while retardants are included to decrease the release rate of hydrophilic agents. The release modulator may be physiologically inert, or a therapeutically active agent.

The rate of release of the therapeutically active agent will be controlled by the rate of transport through the polymeric matrix of the implant, and the action of the modulator. By modulating the release rate, the agent is released at a substantially constant rate, or within a therapeutic dosage range, over the desired period of time. The rate of release will usually not vary by more than about 100% over the desired period of time, more usually by not more than about 50%. The agent is made available to the specific site(s) where the agent is needed, and it is maintained at an effective dosage. The transport of drug through the polymer barrier will also be affected by drug solubility, polymer hydrophilicity, extent of polymer cross-linking, expansion of the polymer upon water absorption so as to make the polymer barrier more permeable to the drug, geometry of the implant, and the like.

The release modulator is an agent that alters the release of a drug from a biodegradable implant in a defined manner. It may be an accelerator or a retardant. Accelerators will be hydrophilic compounds, which are used in combination with hydrophobic agents to increase the rate of release. Hydrophilic agents are those compounds which have at least about 100 µg/ml solubility in water at ambient temperature. Hydrophobic agents are those compounds which have less than about 100 µg/ml solubility in water at ambient temperature.

Therapeutically active hydrophobic agents which benefit from release modulation include cyclosporines, e.g. cyclosporin A, cyclosporin G, etc.; vinca alkaloids, e.g. vincristine and vinblastine; methotrexate; retinoic acid; certain antibiotics, e.g. ansamycins such as rifampin; nitrofurans such as nifuroxazide; non-steroidal antiinflammatory drugs, e.g. diclofenac, ketorolac, flurbiprofen, naproxen, suprofen, ibuprofen, aspirin, etc. Steroids are of particular interest, including hydrocortisone, cortisone, prednisolone, prednisone, dexamethasone, medrysone, fluorometholone, estrogens, progesterones, etc.

Accelerators may be physiologically inert, water soluble polymers, e.g. low molecular weight methyl cellulose or hydroxypropyl methyl cellulose (PMC); sugars, e.g. monosaccharides such as fructose and glucose, disaccharides such as lactose, sucrose, or polysaccharides such as cellulose, amylose, dextran, etc. Alternatively, the accelerator may be a physiologically active agent, allowing for a combined therapeutic formulation. The choice of accelerator in such a case will be determined by the desired combination of therapeutic activities.

Formulations of particular interest will have a therapeutic combination of two or more active agents, which provides for a sustained release of the agents. Combinations may include steroids, as indicated above, as the hydrophobic agent and water soluble antibiotics, e.g. aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity. A combination of non-steroidal anti-inflammatory drugs, as indicated above, with water soluble antibiotics is also of interest. Combinations of anti-viral drugs, e.g. acyclovir, gancyclovir, vidarabine, azidothymidine, dideoxyinosine, dideoxycytosine with steroidal or non-steroidal anti-inflammatory drugs, as indicated above, are of interest. A particular combination of interest is dexamethasone and ciproflaxin.

Release retardants are hydrophobic compounds which slow the rate of release of hydrophilic drugs, allowing for a more extended release profile. Hydrophilic drugs of interest which may benefit from release modulation include water soluble antibiotics, as described above, nucleotide analogs, e.g. acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like.

Agents of interest as release retardants include non-water soluble polymers, e.g. high molecular weight methylcellulose and ethylcellulose, etc., low water soluble organic compounds, and pharmaceutically active hydrophobic agents, as previously described.

A combined anti-inflammatory drug, and antibiotic or antiviral, may be further combined with an additional therapeutic agent. The additional agent may be an analgesic, e.g. codeine, morphine, ketorolac, naproxen, etc., an anesthetic, e.g. lidocaine; β-adrenergic blocker or β-adrenergic agonist, e.g. ephidrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine. Anihelminthic agents, e.g. ivermectin and suramin sodium; antiamebic agents, e.g. chloroquine and chlortetracycline; and antifungal agents, e.g. amphotericin, etc. may be co-formulated with an antibiotic and an anti-inflammatory drug. For intra-ocular use, anti-glaucomas agents, e.g. acetozolamide, befunolol, etc. in combinations with anti-inflammatory and antimicrobial agents are of interest. For the treatment of neoplasia, combinations with anti-neoplastics, particularly vinblastine, vincristine, interferons α, β and γ, antimetabolites, e.g. folic acid analogs, purine analogs, pyrimidine analogs may be used. Immunosuppressants such as azathiprine, cyclosporine and mizoribine are of interest in combinations. Also useful combinations include miotic agents, e.g. carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like.

The amount of active agent employed in the implant, individually or in combination, will vary widely depending on the effective dosage required and rate of release from the implant. Usually the agent will be at least about 1, more usually at least about 10 weight percent of the implant, and usually not more than about 80, more usually not more than about 40 weight percent of the implant. The amount of release modulator employed will be dependent on the desired release profile, the activity of the modulator, and on the release profile of the active agent in the absence of modulator. An agent that is released very slowly or very quickly will require relatively high amounts of modulator. Generally the modulator will be at least 10, more usually at least about 20 weight percent of the implant, and usually not more than about 50, more usually not more than about 40 weight percent of the implant.

Where a combination of active agents is to be employed, the desired release profile of each active agent is determined. If necessary, a physiologically inert modulator is added to precisely control the release profile. The drug release will provide a therapeutic level of each active agent.

The exact proportion of modulator and active agent will be empirically determined by formulating several implants having varying amounts of modulator. A USP approved method for dissolution or release test will be used to measure the rate of release (USP 23; NF 18 (1995) pp. 1790–1798). For example, using the infinite sink method, a weighed sample of the drug delivery device is added to a measured volume of a solution containing four parts by weight of ethanol and six parts by weight of deionized water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released. The drug concentration after 1 h in the medium is indicative of the amount of free unencapsulated drug in the dose, while the time required for 90% drug to be released is related to the expected duration of action of the dose in vivo. Normally the release will be free of larger fluctuations from some average value which allows for a relatively uniform release, usually following a brief initial phase of rapid release of the drug.

Normally the implant will be formulated to release the active agent(s) over a period of at least about 3 days, more usually at least about one week, and usually not more than about one year, more usually not more than about three months. The therapeutically active agent is released within a therapeutic dosage which does not vary by more than about 100% for a period of at least about 3 days. For the most part, the matrix of the implant will have a physiological lifetime at the site of implantation at least equal to the desired period of administration, preferably at least twice the desired period of administration, and may have lifetimes of 5 to 10 times the desired period of administration. The desired period of release will vary with the condition that is being treated. For example, implants designed for post-cataract surgery will have a release period of from about 3 days to 1 week; treatment of uveitis may require release over a period of about 4 to 6 weeks; while treatment for cytomegalovirus infection may require release over 3 to 6 months, or longer.

The implants are of dimensions commensurate with the size and shape of the region selected as the site of implantation and will not migrate from the insertion site following implantation. The implants will also preferably be at least somewhat flexible so as to facilitate both insertion of the implant at the target site and accommodation of the implant. The implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type may be of benefit in some circumstances, where the therapeutic level of the drug falls within a narrow window. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment of at least 7 days, preferably greater than two weeks, water insoluble, and the like. The polymer will usually comprise at least about 10, more usually at least about 20 weight percent of the implant.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. The polymers set forth in Heller, supra, may find use, and that disclosure is specifically incorporated herein by reference.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries.

Among the polysaccharides will be calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137–149.

Particles can be prepared where the center may be of one material and the surface have one or more layers of the same or different composition, where the layers may be cross-linked, of different molecular weight, different density or porosity, or the like. For example, the center would comprise a polylactate coated with a polylactatepolyglycolate copolymer, so as to enhance the rate of initial degradation. Most ratios of lactate to glycolate employed will be in the range of about 1:0.1 to 1:1. Alternatively, the center could be polyvinyl alcohol coated with polylactate, so that on degradation of the polylactate the center would dissolve and be rapidly washed out of the implantation site.

The formulation of implants for use in the treatment of ocular conditions, diseases, tumors and disorders are of particular interest. The biodegradable implants may be implanted at various sites, depending on the shape and formulation of the implant, the condition being treated, etc. Suitable sites include the anterior chamber, posterior chamber, vitreous cavity, suprachoroidal space, subconjunctiva, episcleral, intracorneal, epicorneal and sclera. Suitable sites extrinsic to the vitreous comprise the suprachoroidal space, the pars plana and the like. The suprachoroid is a potential space lying between the inner scleral wall and the apposing choroid. Implants that are introduced into the suprachoroid may deliver drugs to the choroid and to the anatomically apposed retina, depending upon the diffusion of the drug from the implant, the concentration of drug comprised in the implant and the like. Implants may be introduced over or into an avascular region. The avascular region may be naturally occurring, such as the pars plana, or a region made to be avascular by surgical methods. Surgically-induced avascular regions may be produced in an eye by methods known in the art such as laser ablation, photocoagulation, cryotherapy, heat oagulation, cauterization and the like. It may be particularly desirable to produce such an avascular region over or near the desired site of treatment, particularly where the desired site of treatment is distant from the pars plana or placement of the implant at the pars plana is not possible. Introduction of implants over an avascular region will allow for diffusion of the drug from the implant and into the inner eye and avoids diffusion of the drug into the bloodstream.

Figure 3:
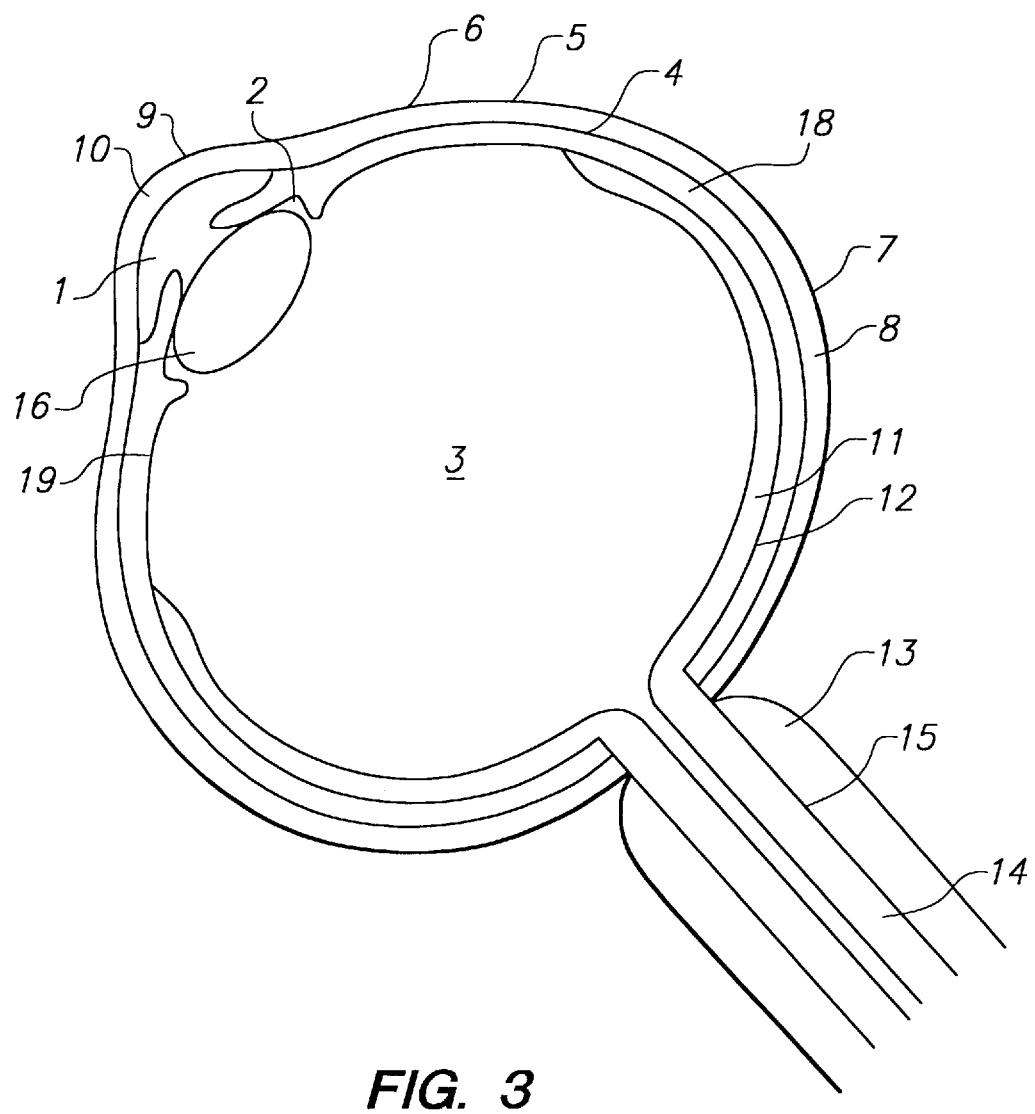
FIG. 3 shows a cross-sectional view of an eye.

Turning now to FIG. 3, a cross-sectional view of the eye is shown, illustrating the sites for implantation in accordance with the subject invention. The eye comprises a lens 16 and encompasses the vitreous chamber 3. Adjacent to the vitreous chamber 3 is the optic part of the retina 11. Implantation may be intraretinal 11 or subretinal 12. The retina is surrounded by the choroid 18. Implantation may be intrachoroidal or suprachoroidal 4. Between the optic part of the retina and the lens, adjacent to the vitreous, is the pars plana 19. Surrounding the choroid 18 is the sclera 8. Implantation may be intrascleral 8 or episcleral 7. The external surface of the eye is the cornea 9. Implantation may be epicorneal 9 or intra-corneal 10. The internal surface of the eye is the conjunctiva 6. Behind the cornea is the anterior chamber 1, behind which is the lens 16. The posterior chamber 2 surrounds the lens, as shown in the figure. Opposite from the external surface is the optic nerves, and the arteries and vein of the retina. Implants into the meningeal spaces 13, the optic nerve 15 and the intraoptic nerve 14 allows for drug delivery into the central nervous system, and provide a mechanism whereby the blood-brain barrier may be crossed.

Other sites of implantation include the delivery of anti-tumor drugs to neoplastic lesions, e.g. tumor, or lesion area, e.g. surrounding tissues, or in those situations where the tumor mass has been removed, tissue adjacent to the previously removed tumor and/or into the cavity remaining after removal of the tumor. The implants may be administered in a variety of ways, including surgical means, injection, trocar, etc.

Other agents may be employed in the formulation for a variety of purposes. For example, buffering agents and preservatives may be employed. Water soluble preservatives which may be employed include sodium bisulfite, sodium bisulfate, odium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition. Where the buffering agent or enhancer is hydrophilic, it may also act as a release accelerator, and may replace all or part of the hydrophilic agent. Similarly, a hydrophilic buffering agent or enhance may replace all or part of the hydrophobic agent.

The implants may be of any geometry including fibers, sheets, films, microspheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3–10 mm×5–10 mm with a thickness of about 0.25–1.0 mm for ease of handling. Where fibers are employed, the diameter of the fiber will generally be in the range of 0.05 to 3 mm. The length of the fiber will generally be in the range of 0.5–10 mm. Spheres will be in the range of 2 µm to 3 mm in diameter.

The size and form of the implant can be used to control the rate of release, period of treatment, and drug concentration at the site of implantation. Larger implants will deliver a proportionately larger dose, but depending on the surface to mass ratio, may have a slower release rate. The particular size and geometry of an implant will be chosen to best suit the site of implantation. The chambers, e.g. anterior chamber, posterior chamber and vitreous chamber, are able to accomodate relatively large implants of varying geometries, having diameters of 1 to 3 mm. A sheet, or circular disk is preferable for implantation in the suprachoroidal space. The restricted space for intraretinal implantation requires relatively small implants, having diameters from 0.5 to 1 mm.

In some situations mixtures of implants may be utilized employing the same or different pharmacological agents. In this way, a cocktail of release profiles, giving a biphasic or triphasic release with a single administration is achieved, where the pattern of release may be greatly varied.

Various techniques may be employed to produce the implants. Useful techniques include solvent evaporation methods, phase separation methods, interfacial methods, extrusion methods, molding methods, injection molding methods, heat press methods and the like. Specific methods are discussed in U.S. Pat. No. 4,997,652, herein incorporated by reference. In a preferred embodiment, extrusion methods are used to avoid the need for solvents in manufacturing. When using extrusion methods, the polymer and drug are chosen so as to be stable at the temperatures required for manufacturing, usually at least about 85° C.

The following examples are offered by way of illustration and not by way of limitation.

EXPERIMENTAL

Example 1

Manufacture and Testing of a Drug Delivery System (DDS) without a Release Modulator Release of the hydrophobic drug dexamethasone from an extended release drug delivery system was measured. The drug delivery system was made with dexamethasone and polylactic acid/polyglycolic acid copolymer. Dexamethasone powder and a powder of polylactic acid polyglycolic acid (PLGA) copolymer were mixed throughly at a ratio of 50/50. The well mixed powder was filled into an extruder, and heated for 1 hour at 95° C., then extruded through a 20 gauge orifice. Six DDS of approximately 100–120 µg were cut from the extruded filaments for drug release assessment.

Each individual DDS was placed in a glass vial filled with receptor medium (9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, each of the glass vials was placed into a shaking water bath at 37° C. Samples were taken for HPLC analysis from each vial at defined time points. The HPLC method was as described in USP 23 (1995) pp. 1791–1798. The concentration values were used to calculate the cumulative release profiles. The release profile is shown in FIG. 1A. It is seen that drug release is very slow with this DDS. Appreciable drug release begins in the fourth week after initiation, at approximately the time of polymer disintegration.

Manufacture and Testing of a DDS with HPMC Release Modifier

A drug delivery system was manufactured as described above, except that various concentrations of hydrophilic hydroxypropylmethylcellulose (HPMC) were included as a release modifier. The combinations of drug, polymer and HPMC shown in Table 1 were used.

TABLE 1

| Lot # | PLGA | HPMC | Dexamethasone | Total |
|-------|------|------|---------------|-------|
| XT014 | 3.5  | 1.5  | 5             | 10    |
| XT015 | 2    | 2    | 5             | 9     |
| XT013 | 1.5  | 1.5  | 5             | 8     |

Figure 1B:
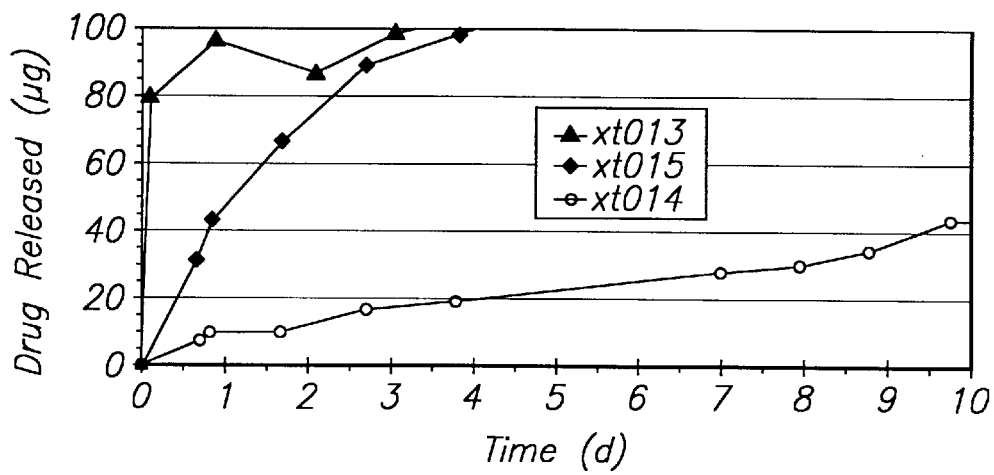
FIG. 1B shows the release profile of the same drug when formulated in a drug delivery system with a release modulator.

The release of drug was tested as described above. The data is shown in FIG. 1B. It is seen that with the addition of HPMC, there is a pronounced increase in the rate of release. Close to zero order release is observed for XT014 and XT015, where the ratio of release modulator to drug is 0.3 to 0.4. By selection of the appropriate polymer and release modifier, drug release and delivery interval can be custom-tailored to provide a release profile that is accelerated or retarded.

Example 2

Manufacture and Testing of A DDS with a Pharmaceutically Active Release Modifier A drug delivery system was manufactured as described in Example 1, except that ciprofloxacin HCl, a pharmaceutically active, hydrophilic compound, was included as a release modifier. The combinations of drug, polymer and HPMC shown in Table 2 were used.

TABLE 2

| Lot # | PLGA | Release Modifier | Drug |
|---|---|---|---|
| XT029 | 5 | — | 5 dexamethasone |
| XT032 | 4 | 2 ciprofloxacin | 4 dexamethasone |
| XT030 | 5 | — | 5 ciprofloxacin |

Figure 2A:
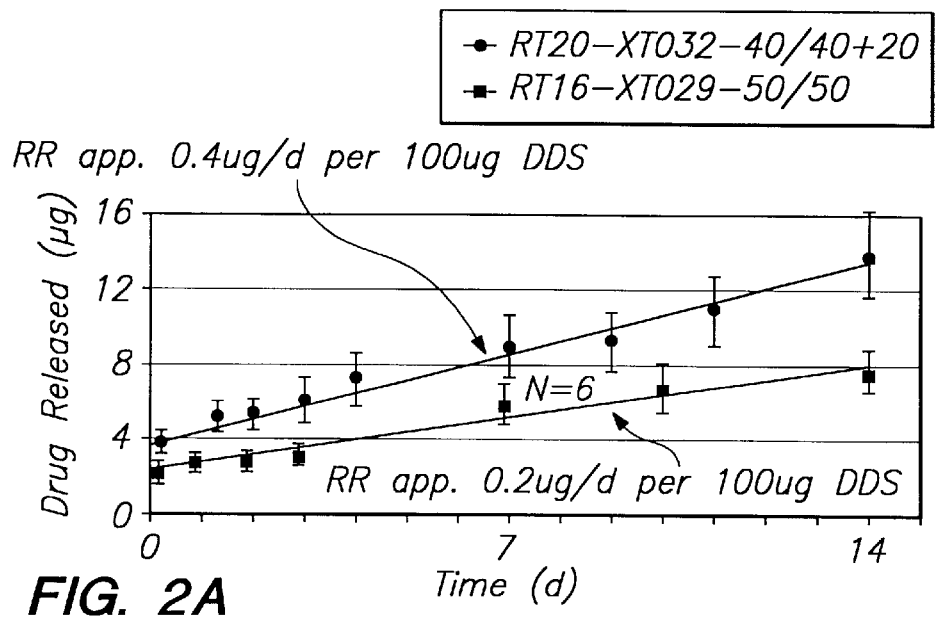
FIG. 2A shows the release profile of dexamethasone in the absence or presence of the release modifier, ciproflaxacin HCl.
Figure 2B:
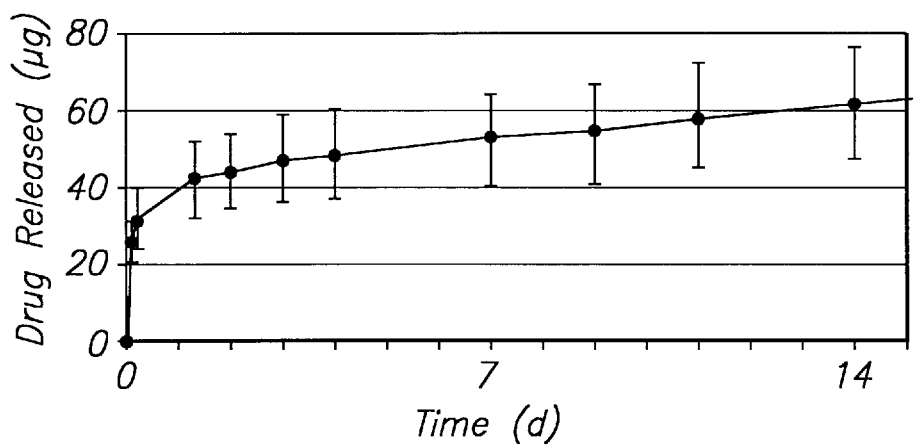
FIG. 2B shows the release of ciprofloxacin in the presence of dexamethasone.
Figure 2C:
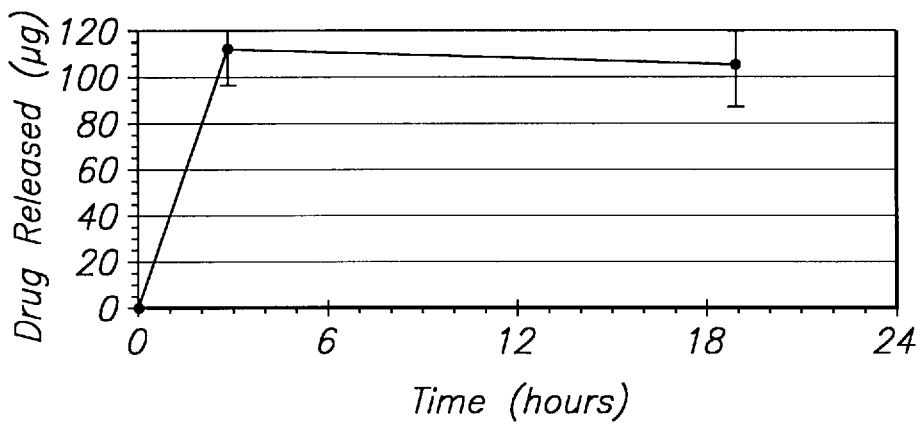
FIG. 2C shows the release of ciprofloxacin in the absence of a release modifier.
Figure 2D:
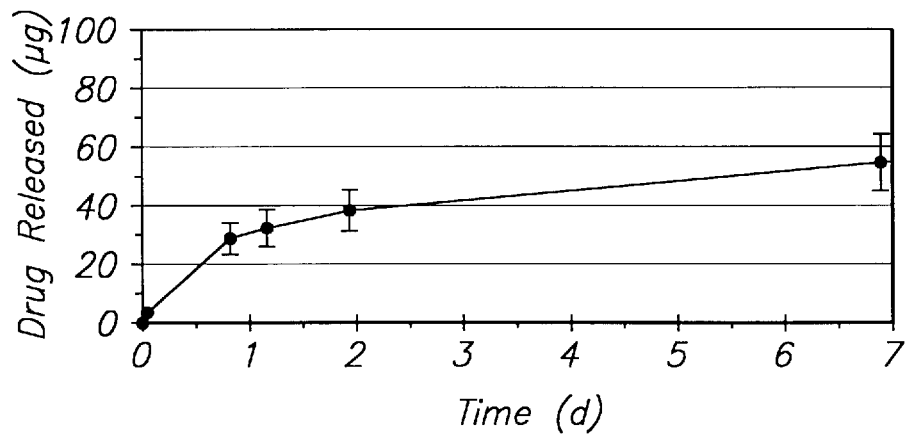
FIG. 2D shows the release profile from a drug delivery system having combined hydrophilic and hydrophobic drugs, and further having a pharmaceutically inactive release modifier.

The release of dexamethasone is increased with the addition of ciprofloxacin HCl, as shown by the data in FIG. 2A. The actual drug release is almost doubled when compared to the DDS without a modifier. In addition to the benefits of increased drug delivery, there are therapeutic benefits introduced with the antibiotic activity of ciprofloxacin. The release of ciprofloxacin from from the same DDS is shown in FIG. 2B. The release rate is higher than that of dexamethasone. However, the overall release of ciprofloxacin is slower when co-formulated with dexamethasone than it is without dexamethasone, as shown in FIG. 2C.

Example 3

Manufacture and Testing of A DDS with Multiple Release Modifiers

A drug delivery system was formulated with hydroxymethylcellulose, cirpofloxacin HCl and dexamethasone, according to the Table 3.

TABLE 3

| Lot # | PLGA | HPMC | Ciprofloxacin | Dexamethasone |
|---|---|---|---|---|
| XT035 | 3.4 | 0.4 | 2.4 | 3.8 |

The data show that after an initial higher release in the first day, an almost zero-order release there after can be observed. The overall release characteristic would be therapeutically acceptable from a therapeutic efficiency aspect.

It is evident from the above results that biodegradable implants formulated with an active agent and release modulator provide for release kinetics where the drug is released at a constant rate over long periods of time, avoiding the need of a patient to administer drugs in much less effective ways, such as topically. The implants provide an improved method of treating ocular and other conditions, by avoiding peaks and troughs of drug release.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An semi-rigid implant for sustained release comprising:

a polyester of lactic acid and glycolic acid in from 10 to 50 weight percent of said implant;

hydroxylpropylmethylcellulose in from 10 to 50 weight percent of said implant; and dexamethasone, wherein said dexamethasone is released within a therapeutic dosage which does not vary by more than about 100% for a period of at least about 3 days.

* * * * *